(12) United States Patent
Yeh et al.

(10) Patent No.: US 9,990,467 B2
(45) Date of Patent: Jun. 5, 2018

(54) ELECTRONIC SYSTEM WITH HEALTH MONITORING MECHANISM AND METHOD OF OPERATION THEREOF

(71) Applicant: Samsung Electronics Co., Ltd., Suwon-si, Gyeonggi-Do (KR)

(72) Inventors: Horng-Li Yeh, Cupertino, CA (US); Truong Nguyen, San Mateo, CA (US); Dan Zhang, Fremont, CA (US); Charles Tang, Scotts Valley, CA (US)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 619 days.

(21) Appl. No.: 14/664,364

(22) Filed: Mar. 20, 2015

(65) Prior Publication Data
US 2016/0117461 A1 Apr. 28, 2016

Related U.S. Application Data

(60) Provisional application No. 62/068,582, filed on Oct. 24, 2014.

(51) Int. Cl.
*G06F 19/00* (2018.01)
(52) U.S. Cl.
CPC ................................ *G06F 19/3412* (2013.01)
(58) Field of Classification Search
CPC .......................... H04L 29/08846; H04L 29/08
See application file for complete search history.

(56) References Cited

U.S. PATENT DOCUMENTS

| | | | | |
|---|---|---|---|---|
| 7,082,528 | B2 * | 7/2006 | Zaudtke | G06F 11/0709 235/462.15 |
| 7,590,522 | B2 * | 9/2009 | Hansen | G06F 3/0626 703/24 |
| 2007/0027981 | A1 | 2/2007 | Coglitore et al. | |
| 2007/0240019 | A1 | 10/2007 | Brady et al. | |
| 2013/0111298 | A1 * | 5/2013 | Seroff | G06F 3/0614 714/758 |

OTHER PUBLICATIONS

JEDEC Solid State Technology Association, "EE1004 and TSE2004 Device Specifications", 2011.
Pecht, M.G., Vichare, N.M., "Prognostics and Health Management of Electronics, Components and Packaging Technologies", IEEE Transactions, vol. 29, Issue 1.

* cited by examiner

*Primary Examiner* — Arvin Eskandarnia
(74) *Attorney, Agent, or Firm* — Perspectives Law Group, Corp.

(57) ABSTRACT

An electronic system includes a control unit configured to generate a firmware register and store a system health information to the firmware register; and a communication unit, coupled to the control unit, configured to retrieve at least a portion of the system health information and communicate the portion of the system health information in response to a singular read request independent of an operational status of a host device.

20 Claims, 7 Drawing Sheets

TEMPERATURE REGISTER ~302

| ADDR | R/W | NAME | FUNCTION | DEFAULT |
|---|---|---|---|---|
| 00 | R | CAPABILITIES | CAPABILITIES OF TEMPERATURE MONITOR | 0X0006 |
| 01 | R/W | CONFIGURATION | TEMPERATURE MONITOR CONFIGURATION | 0X0000 |
| 02 | R/W | HIGH LIMIT | TEMPERATURE HIGH LIMIT | 0X03C0 |
| 03 | R/W | LOW LIMIT | TEMPERATURE LOW LIMIT | 0X0000 |
| 04 | R/W | TCRIT LIMIT | CRITICAL TEMPERATURE | 0X0410 |
| 05 | R | AMBIENT TEMPERATURE | CURRENT AMBIENT TEMPERATURE | N/A |
| 06 | R | MANUFACTURE ID | PCI-SIG MANUFACTURE ID | 0X144D |
| 07 | R | DEVICE ID | PCI-SIG DEVICE ID | 0XA820 |
| 08 ~ 10 | R/W | RSVD ADDR SPACE | RESERVED FUNCTIONS | N/A |

EXAMPLE - REGISTER ADDRESS 08 ⟵ 304

| B15/B7 | B14/B6 | B13/B5 | B12/B4 | B11/B3 | B10/B2 | B9/B1 | B8/B0 |
|---|---|---|---|---|---|---|---|
| N/A | N/A | N/A | N/A | LSTATE-B1 | LSTATE-B2 | LSTATE-B1 | LSTATE-B0 |
| SIGN | 64 | 32 | 16 | 8 | 4 | 2 | 1 |

ELECTRONIC SYSTEM WITH HEALTH MONITORING MECHANISM AND METHOD OF OPERATION THEREOF

CROSS-REFERENCE TO RELATED APPLICATION(S)

This application claims the benefit of U.S. Provisional Patent Application Ser. No. 62/068,582 filed Oct. 24, 2014, the subject matter of which is hereby incorporated by reference herein.

TECHNICAL FIELD

An embodiment of the present invention relates generally to an electronic system, and more particularly to a system with a health monitoring mechanism.

BACKGROUND

Modern consumer and industrial electronics, especially networked-enabled devices are providing increasing levels of functionality to support modern life including facilitating interactions with other electronic devices, appliances, and users. Research and development in the existing technologies can take a myriad of different directions.

As users become more empowered with the growth of networked-enabled devices, new and old paradigms begin to take advantage of the capability to monitor the health, status, and performance of such network-enabled devices. There are many technological solutions to take advantage of this new device monitoring capability. However, current monitoring techniques often rely too heavily on a host device.

Thus, a need still remains for an electronic system with a health monitoring mechanism appropriate for interactions between today's devices. In view of the ever-increasing commercial competitive pressures, along with growing client expectations and the diminishing opportunities for meaningful product differentiation in the marketplace, it is increasingly critical that answers be found to these problems.

Additionally, the need to reduce costs, improve efficiencies and performance, and meet competitive pressures adds an even greater urgency to the critical necessity for finding answers to these problems. Solutions to these problems have been long sought but prior developments have not taught or suggested any solutions and, thus, solutions to these problems have long eluded those skilled in the art.

SUMMARY

An embodiment of the present invention provides an electronic system including a control unit configured to generate a firmware register and store a system health information to the firmware register; and a communication unit, coupled to the control unit, configured to retrieve at least a portion of system health information and communicate the portion of the system health information in response to a singular read request independent of an operational status of a host device.

An embodiment of the present invention provides a method of operation of an electronic system including generating, with a control unit, a firmware register; retrieving at least a portion of system health information; storing the system health information to the firmware register; and communicating the portion of the system health information in response to a singular read request independent of an operational status of a host device.

An embodiment of the present invention provides a non-transitory computer readable medium including generating a firmware register; retrieving at least a portion of system health information; storing the system health information to the firmware register; and communicating the portion of the system health information in response to a singular read request independent of an operational status of a host device.

Certain embodiments of the invention have other steps or elements in addition to or in place of those mentioned above. The steps or elements will become apparent to those skilled in the art from a reading of the following detailed description when taken with reference to the accompanying drawings.

DETAILED DESCRIPTION

Embodiments of the present invention improves the performance of an electronic system by reducing the number of reads a device, such as a host device or a baseboard management controller, has to undertake to obtain a system health information from hardware components of a monitored device. A local system health monitor of the monitored device can reduce the number of reads by serially or sequentially reading the system health information of hardware components of the monitored device. The local system health monitor can serially or sequentially read the system health information based on an event trigger or a timer and store the system health information to a firmware register.

Embodiments of the present invention can also improve the reliability of the electronic system by offloading the monitoring duties from the host device to the local system health monitor. By offloading the monitoring duties from the host device to the local system health monitor, the electronic system can monitor the hardware components of the monitored device without relying on the availability and functions of a host operating system.

Embodiments of the present invention can also improve the efficiency and performance of the electronic system by offloading the management duties from the host device to the local system health monitor. By offloading the management duties from the host device to the local system health monitor, the electronic system can manage the hardware components of the monitored device without relying on an operational status of the host device including the host operating system.

The following embodiments are described in sufficient detail to enable those skilled in the art to make and use the invention. It is to be understood that other embodiments would be evident based on the present disclosure, and that system, process, or mechanical changes may be made without departing from the scope of the present invention.

In the following description, numerous specific details are given to provide a thorough understanding of the invention. However, it will be apparent that the invention may be practiced without these specific details. In order to avoid obscuring the embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation.

Figure 1:
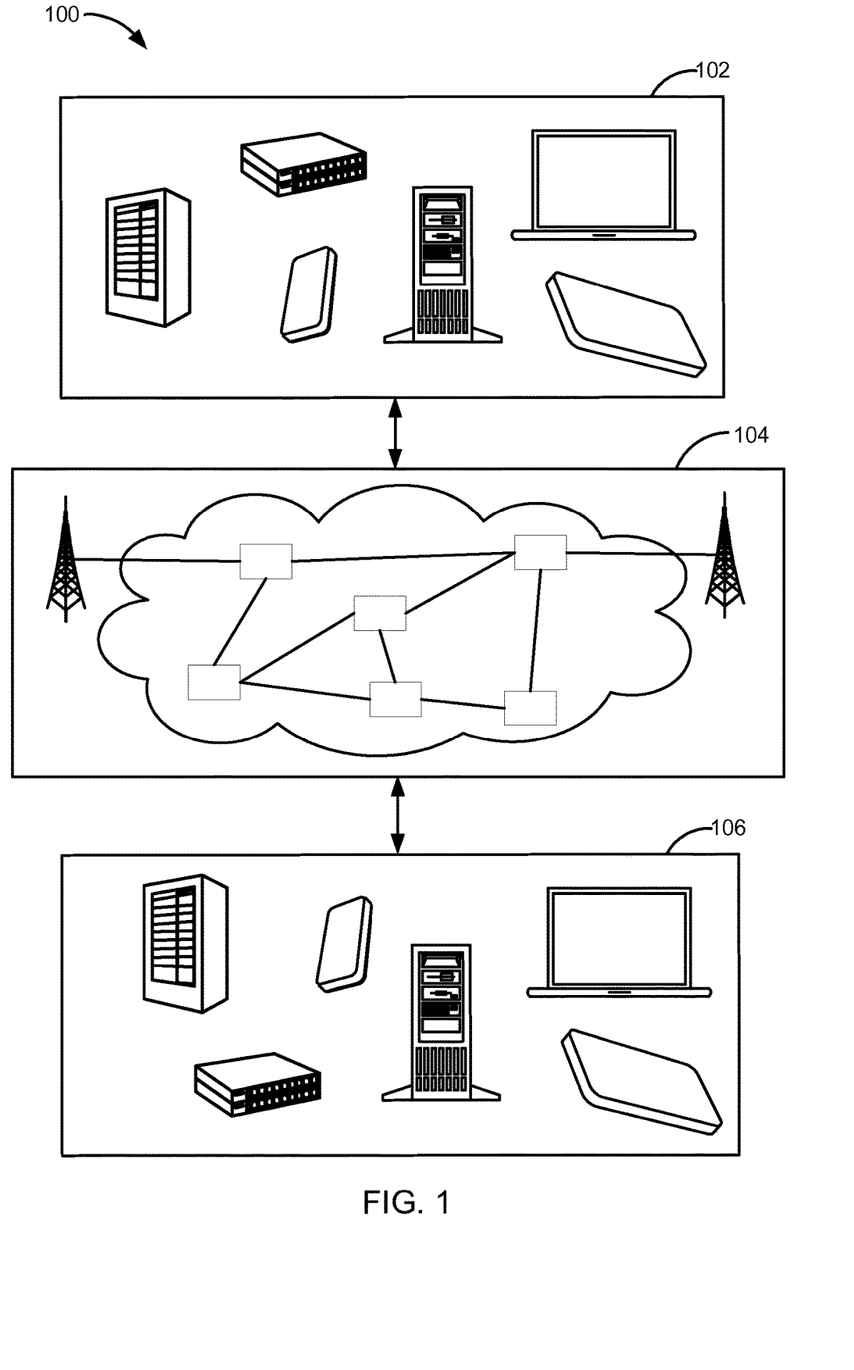
FIG. 1 is an electronic system with a health monitoring mechanism in an embodiment of the present invention.

Referring now to FIG. 1, therein is shown an electronic system 100 with a health monitoring mechanism in an embodiment of the present invention. The electronic system 100 includes a host device 102 connected to a monitored device 106. The host device 102 can communicate with the monitored device 106 with a communication path 104, such as a wireless or wired network.

For illustrative purposes, the electronic system 100 is described with the host device 102 as a separate or discrete device from the monitored device 106, although it is understood that the host device 102 can be included as a component of the monitored device 106 or embedded in the monitored device 106. The host device 102 can be coupled to the communication path 104 to communicate with the monitored device 106.

The host device 102 can be a mobile device or a non-mobile device. For example, the host device 102 can be any of a variety of mobile devices, such as a smartphone, a tablet device, a cellular phone, a wearable device, a notebook computer, a netbook computer, a thin client device, a multi-functional mobile communication or entertainment device, or a combination thereof.

The host device 102 can also be a non-mobile device such as any of a variety of centralized or decentralized monitored devices. For example, the host device 102 can be a desktop computer, a grid computing resource, a server, a server farm, a virtualized computing resource, a cloud computing resource, a router, a switch, a peer-to-peer distributed computing resource, or a combination thereof.

The host device 102 can be centralized in a single computer room, distributed across different rooms, distributed across different geographical locations, or embedded within a telecommunications network. For example, the host device 102 can be a particularized machine, such as a mainframe, a server, a cluster server, a rack mounted server, or a blade server, or as more specific examples, an IBM System z10™ Business Class mainframe or a HP ProLiant ML™ server. The host device 102 can couple with the communication path 104 to communicate with the monitored device 106.

The monitored device 106 can also be a mobile device or a non-mobile device. For example, the monitored device 106 can be any of a variety of mobile devices, such as a smartphone, a tablet device, a cellular phone, a wearable device, a notebook computer, a netbook computer, a thin client device, a multi-functional mobile communication or entertainment device, or a combination thereof.

The monitored device 106 can also be a non-mobile device such as any of a variety of centralized or decentralized monitored devices. For example, the monitored device 106 can be a system component of or embedded in host device 102 (such as a storage drive, an optical drive, a heat-sink, a modem, etc.), or a physically separate device such as a desktop computer, a grid computing resource, a server, a server farm, a virtualized computing resource, a cloud computing resource, a router, a switch, a peer-to-peer distributed computing resource, or a combination thereof.

The monitored device 106 can be centralized in a single machine or computer room, distributed across different rooms, distributed across different geographical locations, or embedded within a telecommunications network. For example, the monitored device 106 can be a particularized machine, such as a mainframe, a server, a cluster server, a rack mounted server, or a blade server, or as more specific examples, an IBM System z10™ Business Class mainframe or a HP ProLiant ML™ server. The monitored device 106 can couple with the communication path 104 to communicate with the host device 102.

Also, for illustrative purposes, the electronic system 100 is shown with the monitored device 106 and the host device 102 as end points of the communication path 104, although it is understood that the electronic system 100 can have a different partition between the host device 102, the monitored device 106, and the communication path 104. For example, the host device 102, the monitored device 106, or a combination thereof can also function as part of the communication path 104.

As a more specific example, the host device 102 can be a management device or component for monitoring a system health, status, or performance of the monitored device 106. In this example, the host device 102 can connect directly to the monitored device 106 through the communication path 104.

As an alternative embodiment not shown in FIG. 1, the monitored device 106 can be included as a component of the host device 102 or embedded in the host device 102. For example, the monitored device 106 can be a system-on-chip, storage drive, modem, optical drive, heat-sink, or integrated circuit embedded in the host device 102 and connected to the host device 102 through a computer bus.

The communication path 104 can be a variety of networks or communication mediums. For example, the communication path 104 can include wireless communication, wired communication, optical communication, or a combination thereof. Satellite communication, cellular communication, Bluetooth™, Bluetooth™ Low Energy (BLE), wireless High-Definition Multimedia Interface (HDMI), ZigBee™, Near Field Communication (NFC), Infrared Data Association standard (IrDA), wireless fidelity (WiFi), and worldwide interoperability for microwave access (WiMAX) are examples of wireless communication that can be included in the communication path 104. Ethernet, HDMI, digital subscriber line (DSL), fiber to the home (FTTH), and plain old telephone service (POTS) are examples of wired communication that can be included in the communication path 104.

Further, the communication path 104 can traverse a number of network topologies and distances. For example, the communication path 104 can include a direct connection, a personal area network (PAN), a local area network (LAN), a metropolitan area network (MAN), a wide area network (WAN) or any combination thereof.

The communication path 104 can also be any variety of wired or fiber optic lines or channels including a serial bus, a parallel bus, or a combination thereof when the host device 102 is included as a component of or embedded in the monitored device 106. For example, the communication path 104 can include, but is not limited to, an Inter- Integrated Circuit (I²C) bus, a System Management Bus (SMBus), a Peripheral Component Interconnect Express (PCI Express) bus, a Serial ATA (SATA) bus, or a combination thereof.

In one specific embodiment, the monitored device 106 can be an embedded or integrated device connected through a direct connection to the host device 102. In this embodiment, the monitored device 106 can be a solid-state drive (SSD) including a Non-Volatile Memory Express (NVMe) SSD in the host device 102. As mentioned above, the host device 102 can be a desktop computer, a grid computing resource, a server, a blade server, a virtualized computing resource, a cloud computing resource, a router, a switch, a peer-to-peer distributed computing resource, a smartphone, a tablet device, a cellular phone, a wearable device, a notebook computer, a netbook computer, a thin client device, a multi-functional mobile communication or entertainment device, or a combination thereof. As will be discussed below, the SSD can communicate health or performance information to a management server representing the host device 102 through an out-of-band bus including, but not limited to, an I²C or SMBus connection.

In another specific embodiment, the monitored device 106 can be a peripheral device external to the host device 102. In this embodiment, the monitored device 106 can also be connected through a direct connection to the host device 102. In yet another specific embodiment, the monitored device 106 can be a device external to the host device 102 and connected to the host device 102 through a network connection including, but not limited to, a storage area network (SAN), a LAN, or a WAN.

Figure 2:
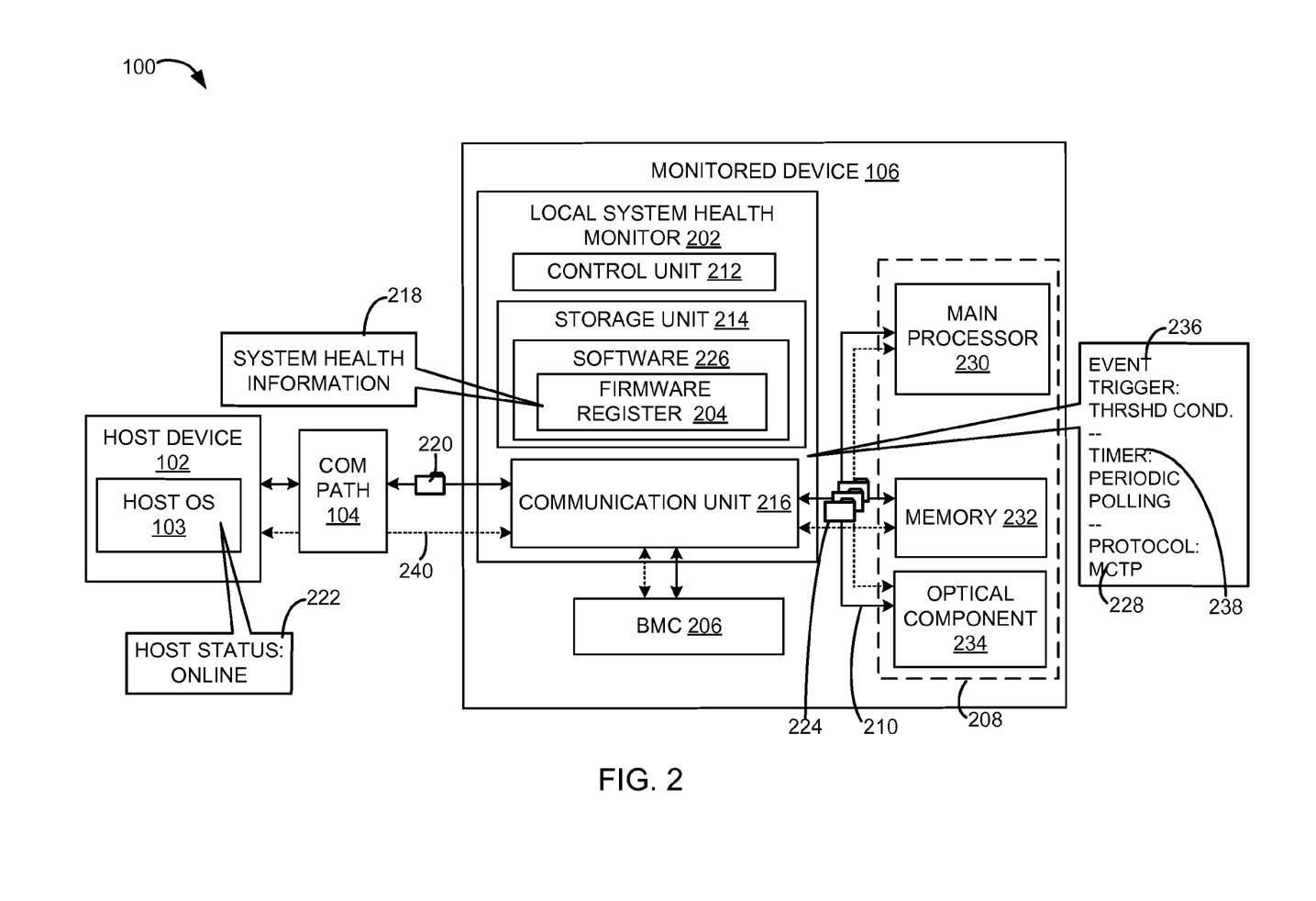
FIG. 2 is an example block diagram of the electronic system.

Referring now to FIG. 2, therein is shown a block diagram of an example embodiment of the electronic system 100. The electronic system 100 can include the host device 102, the communication path 104, and the monitored device 106. The host device 102 can send or receive information in device transmissions over the communication path 104 to the monitored device 106.

For brevity of description in this embodiment of the present invention, the host device 102 will be described as a management device or component and the monitored device 106 will be described as a client device. Embodiments of the present invention are not limited to this selection for the type of devices. The selection is an example of the embodiments of the present invention.

The host device 102 can include a host operating system (OS) 103. The host OS 103 can be a software program for managing the operations of the host device 102. As examples, the host OS 103 can include, but is not limited to, a Windows™ OS, a Mac OS X™, a Linux™ OS, a UNIX OS, an Android™ OS, or a Tizen™ OS. The host OS 103 can maintain an operational status 222 of the host device 102.

The operational status 222 can be a state or condition of a device. The operational status 222 can include, but is not limited to, an active status, an inactive status, a warning status, an online status, an offline status, a maintenance status, a shutdown status, a thermal status, an error status, or a combination thereof.

For example, the operational status 222 of the host device 102 can be inactive when the host OS 103 crashes or stalls. Also, as an example, the operational status 222 of the host device 102 can be offline when a component of the host device 102 malfunctions or is disabled.

The host OS 103 can schedule and undertake operations to determine a health, status, or performance of the monitored device 106. For example, the host OS 103 can schedule a task to retrieve an operating temperature or debug state of a component of the monitored device 106.

The monitored device 106 can include a local system health monitor 202, a baseboard management controller 206, or a combination thereof. In addition, the monitored device 106 can include hardware components 208. Examples of hardware components 208 can include, but are not limited to, a main processor 230, a memory 232, an optical component 234, or a combination thereof. For illustrative purposes, the electronic system 100 is described with the host device 102 as a separate or discrete device from the monitored device 106, although it is understood that the host device 102 can be include the monitored device 106.

The main processor 230 can include, but is not limited to, one or more central processing units (CPUs), graphical processing units (GPUs), Application-Specific Integrated Circuits (ASICs), field-programmable gate arrays (FPGAs), or a combination thereof of the monitored device 106. The main processor 230 can execute software to provide the intelligence of the monitored device 106. The main processor 230 can be implemented in a number of different manners. For example, the main processor 230 can be an embedded processor, a processor core, a microprocessor, a hardware logic, a hardware finite state machine (FSM), a digital signal processor (DSP), or a combination thereof.

The memory 232 can store software, data, logs, or a combination thereof. The memory 232 can be an internal memory, such as the memory 232 depicted in FIG. 2, or an external memory, such as a memory residing on a storage node or a storage server. The memory 232 can be a volatile memory, a non-volatile memory, or a combination thereof. For example, the memory 232 can be a nonvolatile storage such as non-volatile random access memory (NVRAM), Flash memory, disk storage, or a volatile storage such as static random access memory (SRAM). The memory 232 can be the main storage unit for the monitored device 106.

The optical component 234 is a processing or storage unit using light waves or photons for the transmission or storage of data and information. The optical component 234 can include light emitters, modular, detectors, or a combination thereof. The optical component 234 can use fiber optic channels and laser light in lieu of or in combination with electrical components to transmit or store data and information. The optical component 234 can include, but is not limited to, an optical circuit, a photonic integrated circuit, an optoelectronic chip, an optical memory, or a combination thereof.

The baseboard management controller 206 is a specialized processor for monitoring a state of a device or system. The baseboard management controller 206 can monitor the state of the device or system through in-band or out-of-band connections. For example, the baseboard management controller 206 can monitor the state of the device or system through a sideband connection such as a System Management Bus (SMBus).

In addition, the baseboard management controller 206 can monitor the temperature, humidity, power-supply voltage, or fan speed of a device or component. Also for example, the motherboard or main circuit board of the monitored device 106 can include the baseboard management controller 206.

For illustrative purposes, the monitored device 106 and the host device 102 is shown with the partition depicted in FIG. 2, although it is understood that the monitored device 106 and the host device 102 can have a different partition. For example, as described above, the monitored device 106 can be an embedded or integrated device in the host device 102. In one example embodiment, the monitored device 106 can be a storage device, such as a SSD, in the host device 102. In another example embodiment, the monitored device 106 can be a device external to the host device 102 and connected to the host device 102 through a network connection including, but not limited to, a storage area network (SAN), a LAN, or a WAN.

In one or more embodiments, the baseboard management controller 206 can be a standalone device outside of the monitored device 106. Also, in these and other embodiments, the baseboard management controller 206 can be a component in the host device 102.

The local system health monitor 202 can include a control unit 212, a storage unit 214, a communication unit 216, or a combination thereof. The control unit 212 can execute a software 226 to provide the intelligence of the local system health monitor 202. The control unit 212 can be implemented in a number of different ways.

For example, the control unit 212 can be a processor, a processor core, an embedded processor, a microprocessor, a hardware control logic, a hardware finite state machine (FSM), a digital signal processor (DSP), or a combination thereof. The control unit 212 can use a control interface to communicate with other functional units in the local system health monitor 202.

The storage unit 214 can store the software 226 for the local system health monitor 202 including a firmware register 204. The storage unit 214 can be a volatile memory, a nonvolatile memory, an internal memory, an external memory, or a combination thereof. For example, the storage unit 214 can be a nonvolatile storage such as a non-volatile random access memory (NVRAM), Flash memory, disk storage, or a volatile storage such as static random access memory (SRAM).

The firmware register 204 is a register space emulated in firmware. The firmware register 204 can include an address space of memory location(s) where data is stored. The firmware register 204 can be accessed by the control unit 212 of the local system health monitor 202 or other devices external to the local system health monitor 202. The firmware register 204 will be discussed in more detail below.

The communication unit 216 can enable external communication to and from the local system health monitor 202. For example, the communication unit 216 can permit the local system health monitor 202 to communicate with the communication path 104, the host device 102, the baseboard management controller 206, the hardware components 208, or a combination thereof.

The communication unit 216 can communicate with the baseboard management controller 206, the hardware components including the main processor 230, the memory 232, the optical component 234, or a combination thereof through device buses 210. The device buses 210 can include any variety of wired or optical lines or channels including a serial bus, a parallel bus, a fiber optic connection, or a combination thereof. For example, the device buses 210 can include, but are not limited to, an Inter-Integrated Circuit (I²C) bus, a SMBus, a Peripheral Component Interconnect Express (PCI Express) bus, a Serial ATA (SATA) bus, or a combination thereof.

The device buses 210 can include an in-band bus and an out-of-band bus 240. The out-of-band bus 240 can be a communication bus outside of the normal data path. The out-of-band bus 240 can include a sideband bus.

The communication unit 216 can also function as a communication hub allowing the local system health monitor 202 to function as part of the communication path 104 and not limited to be an end point or terminal unit of the communication path 104. The communication unit 216 can include active and passive components, such as microelectronics or an antenna, for interaction with the communication path 104. The communication unit 216 can also communicate with other wired or wireless connections of the monitored device 106.

As will be discussed more below, the local system health monitor 202 can retrieve at least a portion of system health information 218. The system health information 218 is data or information indicating a health or performance metric of one or more of the hardware components 208 of a device. The system health information 218 can include information concerning, but not limited to, a temperature, a humidity, a power-supply voltage, or a fan speed of the hardware components 208 or subcomponents therein.

The local system health monitor 202 can retrieve at least the portion of the system health information 218 from multiple reads 224 of the hardware components 208 of the monitored device 106. The local system health monitor 202 can undertake the multiple reads 224 by accessing or querying the hardware components 208 sequentially or serially.

The local system health monitor 202 can retrieve at least the portion of the system health information 218 based on an event trigger 236, a timer 238, or a combination thereof. The event trigger 236 is a retrieval process automatically initiated when a condition or threshold is met. The local system health monitor 202 can retrieve at least the portion of the system health information 218 from the hardware components 208 based on one or more instances of the event trigger 236 being met.

The event trigger 236 can include a sensor condition or threshold, a performance condition or threshold, an error, a latency threshold, or a combination thereof. For example, the event trigger 236 can include the main processor 230 exceeding a suggested temperature range. As another example, the event trigger 236 can include an error associated with an operation of the memory 232. Also, the event trigger 236 can include a performance problem associated with the host device 102.

The timer 238 is a retrieval process called or executed on a periodic or scheduled basis. The timer 238 can include a polling procedure such as a periodic polling of the hardware components 208. For example, the local system health monitor 202 can retrieve at least the portion of the system health information 218 by periodically polling the main processor 230, the memory 232, the optical component 234, or a combination thereof.

The local system health monitor 202 can retrieve at least the portion of the system health information 218 over the device buses 210 through a number of communication protocols. Examples of the communication protocols include a management component transport protocol (MCTP) 228, a SMBus protocol, a PCI Express protocol, a SATA protocol, or a combination thereof.

The local system health monitor 202 can also communicate the portion of the system health information 218 in response to a singular read request 220 received by the local system health monitor 202. The singular read request 220 can be a read of the firmware register 204 without reading the hardware components 208 of the monitored device 106.

The singular read request 220 can include a query, function call, or command received by the communication unit 216 of the local system health monitor 202 for accessing information stored in the firmware register 204. For example, the singular read request 220 can include one or more reads of the firmware register 204 without reading the hardware components 208 of the monitored device 106.

The singular read request 220 can be initiated by another device in the electronic system 100 including the host device 102. In other embodiments of the present invention, the singular read request 220 can be initiated by the control unit 212 of the local system health monitor 202. In addition, the singular read request 220 can be initiated by the baseboard management controller 206 for reading information from the firmware register 204.

As will be discussed more below, the local system health monitor 202 can communicate the portion of the system health information 218 in response to the singular read request 220 received by the local system health monitor 202 independent of the operational status 222 of the host device 102. For illustrative purposes, the electronic system 100 is described by operation of the local system health monitor 202. Although, it is understood that the baseboard management controller 206, the main processor 230, the memory 232, the optical component 234, or a combination thereof of the monitored device 106 can also operate any of the steps and functions of the electronic system 100. For example, the control unit 212 of the local system health monitor 202 is described to execute the software 226, including the emulation of the firmware register 204, although it is understood that the main processor 230, the baseboard management controller 206, or a combination thereof of the monitored device 106 can also execute the software 226. As an additional example, the firmware register 204 can also be stored in the memory 232.

Also, in other example embodiments, the software 226 can be partitioned differently such that some or all of its function can be in the storage unit 214 of the local system health monitor 202 and the memory 232. The host device 102, the monitored device 106, or a combination thereof can include other functional units not shown in FIG. 2 for clarity. The functional units in the monitored device 106 can work individually and independently of the other functional units. The monitored device 106 can also work individually and independently from the host device 102 and the communication path 104.

Figure 3:
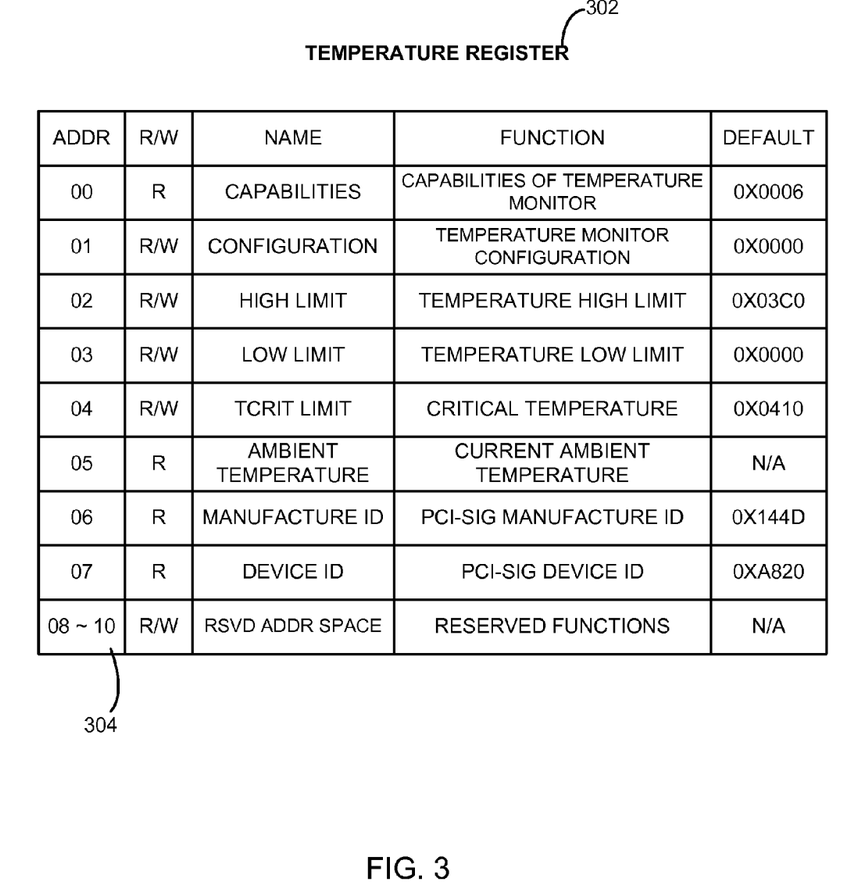
FIG. 3 is an example diagram of a firmware register.

Referring now to FIG. 3, therein is shown an example diagram of the firmware register 204 of FIG. 2. The firmware register 204 can be generated by the local system health monitor 202 of FIG. 2. The local system health monitor 202 can generate the firmware register 204 by emulating a processor register such as a status register, an interrupt register, a control register, or a combination thereof using the firmware register 204. As a more specific example, the firmware register 204 can include, but is not limited to, a memory address register (MAR), a memory buffer register (MBR), an instruction register (IR), a pointer register, a program counter (PC), or a combination thereof. Moreover, the firmware register 204 can emulate an 8-bit register, a 16-bit register, a 32-bit register, or a combination thereof. In addition, the local system health monitor 202 can also emulate a system register such as a temperature register 302, a debug register, or a combination thereof.

For illustrative purposes, the firmware register 204 is depicted as the temperature register 302, although it is understood that the firmware register 204 can be any type or class of registers. For example, the firmware register 204 can be an instance of the temperature register 302 complying with the Joint Electronic Device Engineering Council (JEDEC) Solid State Technology Association's EE1004 and TSE2004 Device Specifications. As another example, the firmware register 204 can be an instance of the temperature register 302 complying with the JEDEC Solid State Technology Association's TSE2002 Device Specifications. As more specific examples, the firmware register 204 can be a TSE2002av or TSE2004av compliant temperature register.

As depicted in FIG. 3, address 00 of the firmware register 204 can be used as a capabilities register. The capabilities register can be a read-only register indicating the supported features of a sensor such as a temperature sensor. In addition, address 01 of the firmware register 204 can be used as a configuration register for holding the control and status bits of an event pin as well as general hysteresis on all limits. Furthermore, addresses 02, 03 and 04 can be used as a high limit register, a low limit register, and a temperature critical register, respectively for defining the temperatures to be used by various on-chip comparators to determine device temperature status and thermal events.

Moreover, address 05 can be used as a temperature data register for holding data concerning internal temperature measurements as well as status bits indicating which error conditions, if any, are active. Addresses 06 and 07 can be used as a manufacturer ID register and a device ID register, respectively, for holding identifying information concerning the specific manufacturer and the monitored device 106.

The firmware register 204 can also include a reserved address space 304. The reserved address space 304 is a set of memory addresses set aside for monitoring or maintaining a health, status, or performance of the monitored device 106. The reserved address space 304 can be set aside for functional tasks dictated by a device manufacturer, including an original equipment manufacturer (OEM) or a vendor.

For illustrative purposes, the reserved address space 304 is shown as address spaces 08 to 10, although it is understood that the reserved address space 304 can span any number of memory addresses as dictated by a device manufacturer. The reserved address space 304 will be discussed in more detail below.

In one specific embodiment, TSE2002av or TSE 2004av temperature registers supported in all compliant hardware sensors can be emulated in firmware. In this embodiment, the vendor-defined registers can be used to convey device health information which can be accessed through the out-of-band bus 240.

Figure 4:
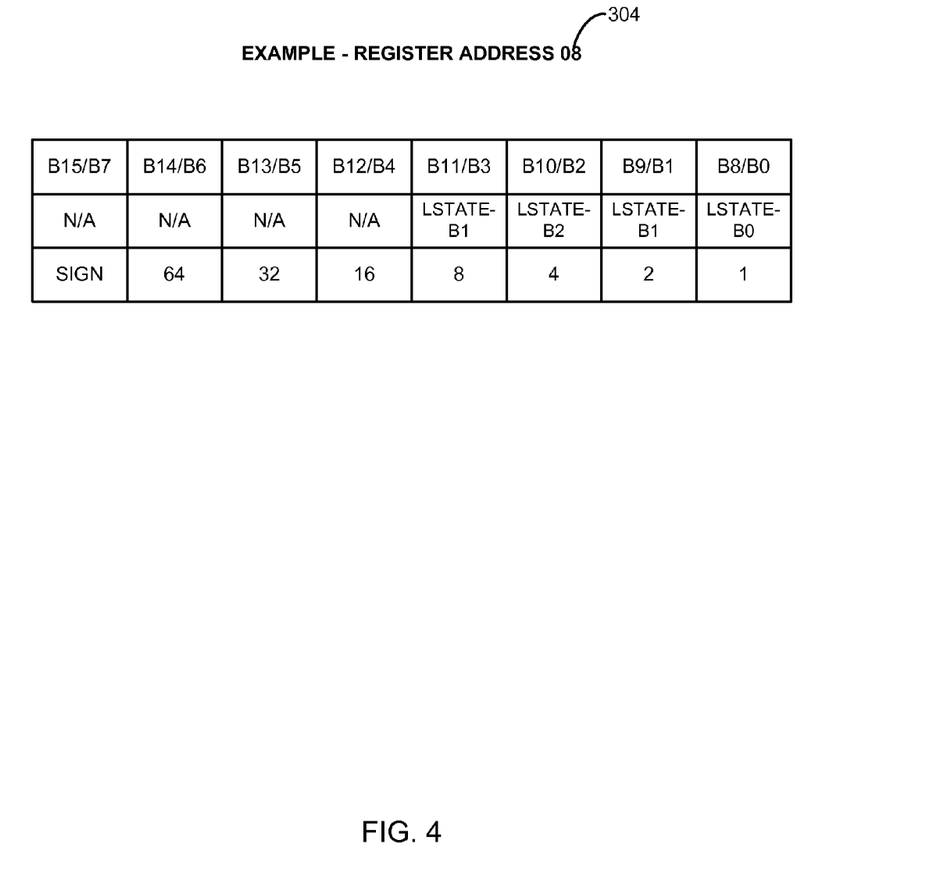
FIG. 4 is an example diagram of a reserved address space of a firmware register.

Referring now to FIG. 4, therein is shown an example of the reserved address space 304 of the firmware register 204 of FIG. 3. The reserved address space 304 can be used to convey a health, status, or performance information of one of the hardware components 208 of FIG. 2. For example, as depicted in FIG. 4, the reserved address space 304 can be used to consolidate a light emitting diode (LED) register and an ambient temperature register. The LED register can be used to communicate the portion of the system health information 218 of FIG. 2 through an LED array for notifying or alerting a user or network administrator of a health or performance of the hardware components 208.

In a more specific embodiment, the reserved address space 304 can be a 16-bit register with the lower 8-bits of the reserved address space 304 used to convey an ambient temperature of one of the hardware components 208. In addition, the upper 8-bits of the reserved address space 304 can be used to convey other health, status, or performance information.

Figure 5:
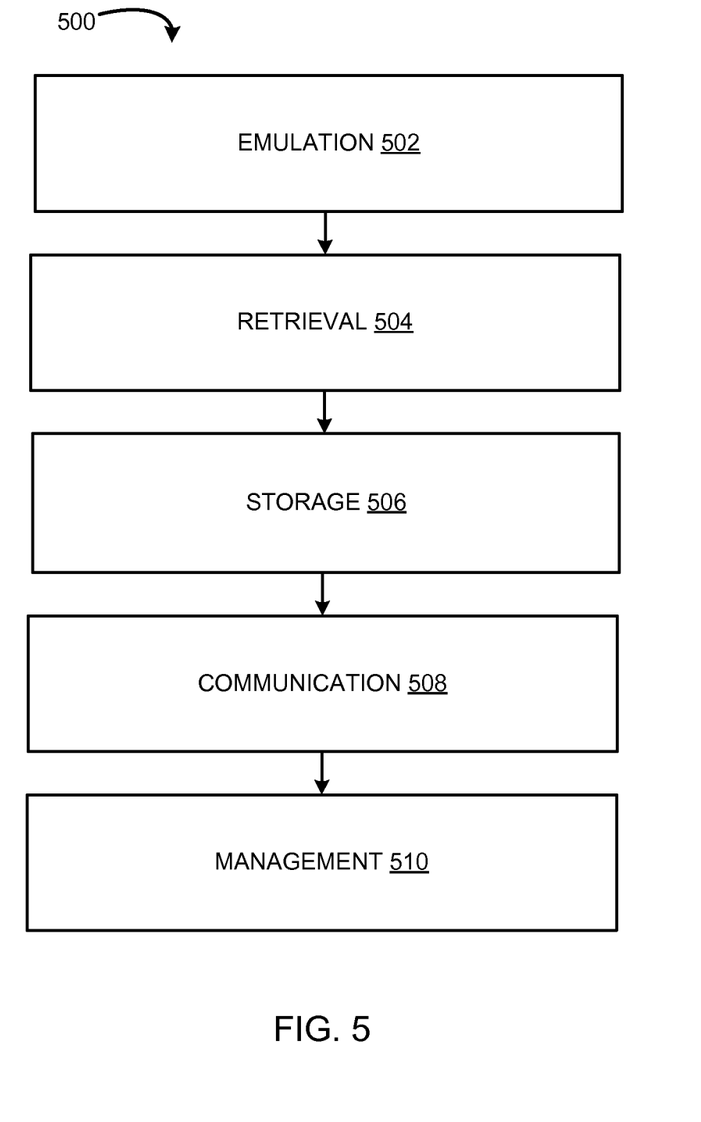
FIG. 5 is a control flow of the electronic system.

Referring now to FIG. 5, therein is shown a control flow 500 of the electronic system 100 of FIG. 1. The electronic system 100 can include an emulation step 502, a retrieval step 504, a storage step 506, a communication step 508, a management step 510, or a combination thereof.

The emulation step 502 includes generating, with the control unit 212 of FIG. 2 of the local system health monitor 202 of FIG. 2, the firmware register 204 of FIG. 2. The control unit 212 can generate the firmware register 204 by emulating one or more registers of a device in the electronic system 100. The control unit 212 can generate the firmware register 204 by emulating one or more registers of the monitored device 106 of FIG. 1.

In one example embodiment, the control unit 212 can generate the firmware register 204 by emulating the temperature register 302 of FIG. 3 of the monitored device 106 in firmware. The control unit 212 can generate the firmware register 204 by emulating one or more hardware memory locations associated with the hardware components 208 of FIG. 2. The control unit 212 can also emulate a control register, an interrupt register, a status register, or a combination thereof in firmware. The control unit 212 can generate the firmware register 204 by making sensor or interface outputs accessible to the local system health monitor 202, the host device 102 of FIG. 1, the baseboard management controller 206 of FIG. 2, or a combination thereof as a readable file.

The emulation step 502 can also include generating the firmware register 204 by emulating the reserved address space 304 of FIG. 3 in firmware. The control unit 212 of the local system health monitor 202 can emulate the reserved address space 304 for a device in the electronic system 100. The control unit 212 can emulate the reserved address space 304 for the host device 102 of FIG. 1. In other example embodiments of the present invention, the control unit 212 can emulate the reserved address space 304 for the baseboard management controller 206.

In addition, the emulation step 502 can include reserving a portion of the system address space of the electronic system 100 for the firmware register 204. The control unit 212 can store the firmware register 204 in the storage unit 214 of FIG. 2. In other embodiments of the present invention, the control unit 212 can store the firmware register 204 in the memory 232 of FIG. 2.

The emulation step 502 can be implemented as instructions of the software 226 of FIG. 2. The control unit 212 can execute the software 226 to generate the firmware register 204. The emulation step 502 can also be implemented as hardware circuitry or hardware accelerators in the control unit 212. In addition, the emulation step 502 can also be implemented as hardware circuitry or hardware accelerators outside of the control unit 212, including in the main processor 230. After generating the firmware register 204, the control flow 500 can pass to the retrieval step 504.

The retrieval step 504 includes retrieving the system health information 218 of FIG. 2 concerning the hardware components 208. The local system health monitor 202 can retrieve at least the portion of the system health information 218 for determining a health, status, or performance of the hardware components 208, the host device 102, the baseboard management controller 206, subcomponents therein, or combinations thereof. The local system health monitor 202 can use the communication unit 216 of FIG. 2 to retrieve the system health information 218 from the hardware components 208.

The communication unit 216 can retrieve at least the portion of the system health information 218 from the multiple reads 224 of FIG. 2 of the hardware components 208. The multiple reads 224 can refer to the communication unit 216 accessing or querying the hardware components 208 sequentially or serially.

For example, the local system health monitor 202 can use the communication unit 216 to first read the temperature of the main processor 230 of FIG. 2 followed by the temperature of the memory 232 and then followed by the temperature of the optical component 234 of FIG. 2. As a more specific example, the local system health monitor 202 can use the communication unit 216 to read the outputs from one or more temperature sensors coupled to the main processor 230, the memory 232, the optical component 234, or a combination thereof.

The communication unit 216 of the local system health monitor 202 can retrieve at least the portion of the system health information 218 from the hardware components 208 using the device buses 210 of FIG. 2. In one embodiment, the communication unit 216 can retrieve at least the portion of the system health information 218 through the out-of-band bus 240 of FIG. 2 including the sideband bus. For example, the communication unit 216 can retrieve at least the portion of the system health information 218 through a SMBus. The out-of-band bus 240 can include an instance of the device buses 210 outside of the normal data path.

In another embodiment, the communication unit 216 can also retrieve the system health information 218 through an in-band bus. The in-band bus can include an instance of the device buses 210 of FIG. 2 in the normal data path. For example, the communication unit 216 can retrieve at least the portion of the system health information 218 through the in-band bus during periods of low activity or inactivity.

The local system health monitor 202 can also use the communication unit 216 to retrieve the system health information 218 through an $I^2C$ bus, a PCI Express bus, a SATA bus, or a combination thereof. The local system health monitor 202 can retrieve at least the portion of the system health information 218 using the management component transport protocol 228 of FIG. 2. In other embodiments of the present invention, the local system health monitor 202 can retrieve at least the portion of the system health information 218 using other communication protocols including the SMBus protocol, the PCI Express protocol, the SATA protocol, or a combination thereof.

The local system health monitor 202 can retrieve at least the portion of the system health information 218 independent of the operational status 222 of FIG. 2 of the host device 102. For example, the local system health monitor 202 can retrieve at least the portion of the system health information 218 when the host device 102 is offline or undergoing maintenance.

The local system health monitor 202 can retrieve at least the portion of the system health information 218 based on the event trigger 236 of FIG. 2, the timer 238 of FIG. 2, or a combination thereof. The local system health monitor 202 can retrieve at least the portion of the system health information 218 based on the event trigger 236 when a condition or threshold is met. For example, the local system health monitor 202 can read a temperature sensor of the main processor 230 when the temperature of the main processor 230 exceeds a manufacturer recommended temperature range.

The local system health monitor 202 can also retrieve the system health information 218 based on the timer 238. For example, the local system health monitor 202 can periodically poll the temperature sensor of the main processor 230, the memory 232, the optical component 234, or a combination thereof.

The retrieval step 504 can be implemented as instructions of the software 226. The control unit 212 can execute the software 226 to retrieve the system health information 218. The retrieval step 504 can also be implemented as hardware circuitry or hardware accelerators in the control unit 212. In addition, the retrieval step 504 can also be implemented as hardware circuitry or hardware accelerators outside of the control unit 212, including in the main processor 230. After retrieving the system health information 218, the control flow 500 can pass to the storage step 506.

The storage step 506 includes storing the system health information 218 to the firmware register 204. The local system health monitor 202 can store the system health information 218 to the reserved address space 304 of FIG. 3 of the firmware register 204.

The firmware register 204 can be stored in the storage unit 214. The local system health monitor 202 can store the system health information 218 in a non-volatile memory of the monitored device 106. The local system health monitor 202 can store the system health information 218 obtained from the multiple reads 224 of the hardware components 208.

As a more specific example, the firmware register 204 can include the temperature register 302 of FIG. 3. The local system health monitor 202 can retrieve temperature data concerning the hardware components 208 including the main processor 230, the memory 232, the optical component 234, or a combination thereof from the multiple reads 224. The local system health monitor 202 can then use the storage unit 214 to store the temperature data representing the system health information 218 concerning the main processor 230, the memory 232, the optical component 234, or a combination thereof in the firmware register 204.

The storage step 506 can be implemented as instructions of the software 226. The control unit 212 can execute the software 226 to store the system health information 218. The storage step 506 can also be implemented as hardware circuitry or hardware accelerators in the control unit 212. In addition, the storage step 506 can also be implemented as hardware circuitry or hardware accelerators outside of the control unit 212, including in the main processor 230. After storing the system health information 218, the control flow 500 can pass to the communication step 508.

The communication step 508 includes communicating, with the communication unit 216 of FIG. 2, the system health information 218 in response to the singular read request 220 of FIG. 2 received by the local system health monitor 202. The communication step 508 can include communicating the portion of the system health information 218 in response to the singular read request 220 independent of the operational status 222 of the host device 102.

The local system health monitor 202 can communicate the portion of the system health information 218 by communicating the portion of the system health information 218 to the host device 102. The local system health monitor 202 can also communicate the portion of the system health information 218 to other devices in the electronic system 100. Moreover, the local system health monitor 202 can also communicate the portion of the system health information 218 to the baseboard management controller 206.

The local system health monitor 202 can communicate the portion of the system health information 218 to the host device 102 in response to the firmware register 204 receiving the singular read request 220. The singular read request 220 can be a single query or function call received by the local system health monitor 202 for accessing information stored in the firmware register 204. The singular read request 220 can be initiated by the host device 102. The singular read request 220 can also be initiated by other devices in the electronic system 100 including a device other than the host device 102. For example, the singular read request 220 can be initiated by another plug-in card of the monitored device 106. In addition, the singular read request 220 can also be initiated by the local system health monitor 202 itself.

Moreover, the singular read request 220 can be initiated by the baseboard management controller 206.

The local system health monitor 202 can communicate the portion of the system health information 218 to another device in the electronic system 100 independent of the operational status 222 of the host device 102. For example, the local system health monitor 202 can communicate the portion of the system health information 218 to another device in the electronic system 100 when the host OS 103 is stalling or crashing. As a more specific example, the local system health monitor 202 can communicate the portion of the system health information 218 to the baseboard management controller 206 when the host OS 103 is stalling or crashing. As another example, the local system health monitor 202 can communicate the portion of the system health information 218 to the host device 102 when the host device 102 is undergoing maintenance.

The local system health monitor 202 can use the communication unit 216 to communicate the portion of the system health information 218 to another device in the electronic system 100 over the communication path 104. The local system health monitor 202 can also use the communication unit 216 to communicate the portion of the system health information 218 to another component of the monitored device 106 over the device buses 224.

The local system health monitor 202 can also communicate the portion of the system health information 218 through a user interface (not shown) of the monitored device 106. For example, the local system health monitor 202 can communicate the portion of the system health information 218 through a light emitting diode (LED) array for notifying or alerting a user or network administrator of a health or performance of one of the hardware components 208.

The communication step 508 can be implemented as instructions of the software 226. The control unit 212 can execute the software 226 to communicate the portion of the system health information 218. The communication step 508 can also be implemented as hardware circuitry or hardware accelerators in the control unit 212. In addition, the communication step 508 can also be implemented as hardware circuitry or hardware accelerators outside of the control unit 212, including in the main processor 230. After communicating the portion of the system health information 218, the control flow 500 can pass to the management step 510.

It has been discovered that storing the system health information 218 to the firmware register 204 and communicating the portion of the system health information 218 in response to the singular read request 220 improves the performance of the electronic system 100. Further, the firmware register 204 and the response to the singular read request 220 can reduce the number of reads by a device, such as the host device 102 or the baseboard management controller 206, to obtain the system health information 218. The electronic system 100 can reduce the number of reads by allowing the local system health monitor 202 to serially or sequentially read the system health information 218 of the hardware components 208 based on the event trigger 236 or the timer 238 and store the system health information 218 to the firmware register 204 for reading by another device or component.

It has been discovered that communicating the portion of the system information 218 in response to the singular read request 220 received by the local system health monitor 202 independent of the operational status 222 of the host device 102 improves the reliability of the electronic system 100 by offloading the monitoring duties of the host device 102 to the local system health monitor 202. By offloading the monitoring duties of the host device 102 to the local system health monitor 202, the electronic system 100 can monitor the hardware components 208 of the monitored device 106 without relying on the availability and functions of the host OS 103.

The management step 510 includes managing, with the control unit 212, the hardware components 208 independent of the operational status 222 of the host device 102. The local system health monitor 202 can manage the hardware components 208 in response to the system health information 218 read from the hardware components 208.

The local system health monitor 202 can manage the hardware components 208 by first diagnosing a problem exhibited by the hardware components 208. The local system health monitor 202 can then manage the hardware components 208 by shutting down, rebooting, power cycling, or debugging the hardware components 208. The local system health monitor 202 can manage the hardware components 208 without input from the host device 102. The local system health monitor 202 can also interact with the baseboard management controller 206 to manage the hardware components 208.

In other embodiments, the local system health monitor 202 can also manage the host device 102. The local system health monitor 202 can manage the host device 102 by shutting down, rebooting, power cycling, or debugging the host device 102. For example, the local system health monitor 202 can manage the host device 102 by sending an interrupt to the host device 102 to break a loop stalling the host device 102.

The management step 510 can be implemented as instructions of the software 226. The control unit 212 can execute the software 226 to manage the hardware components 208. The management step 510 can also be implemented as hardware circuitry or hardware accelerators in the control unit 212. In addition, the management step 510 can also be implemented as hardware circuitry or hardware accelerators outside of the control unit 212, including in the main processor 230.

It has been discovered that managing the hardware components 208 using the system hardware monitor 202 improves the efficiency and performance of the electronic system 100 by offloading the management duties of the host device 102 to the local system health monitor 202. By offloading the management duties of the host device 102 to the local system health monitor 202, the electronic system 100 can manage the hardware components 208 of the monitored device 106 without relying on the operational status 222 of the host device 102 including the host OS 103.

It has been discovered that one advantage of the local system health monitor 202 is that it is a cost effective way to integrate into an existing device environment. In addition, the local system health monitor 202 can support a set of devices, including servers, in a "lights out" device environment.

Figure 6:
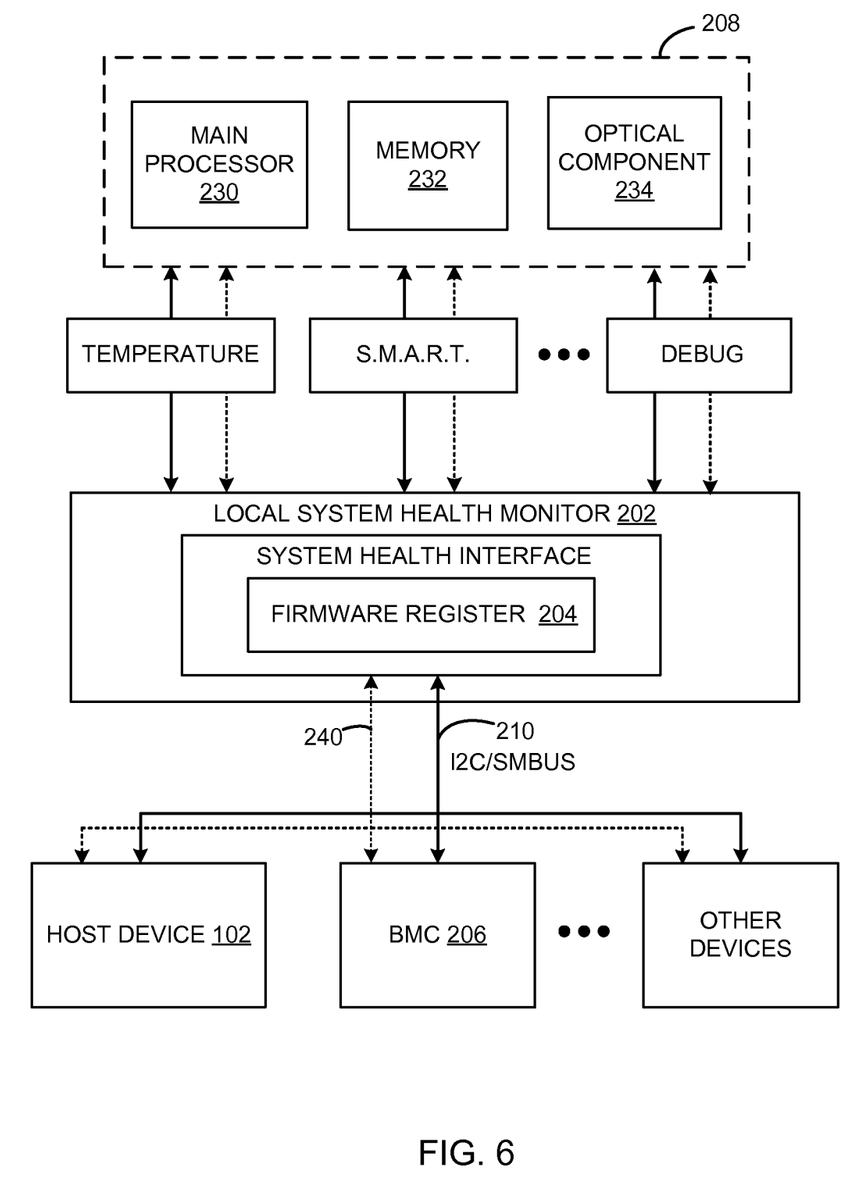
FIG. 6 is an example diagram of the firmware register in operation.

Referring now to FIG. 6, therein is shown an example diagram of the firmware register 204 in operation. As depicted in FIG. 6, the firmware register 204 can be part of a system health interface such as a TSE 2002av or a TSE 2004av interface. As a more specific example, the system health interface can be a TSE2002/TSE2004av compliant temperature register such as the temperature register 302 of FIG. 3.

The local system health monitor 202 can provide information with regard to a temperature state, a debug state, or a Smart-Monitoring, Analysis and Reporting Technology (S.M.A.R.T.) warning state through the system health interface. This information can be consolidated into the reserved address space 304 of FIG. 3 of the firmware register 202.

The local system health monitor 202 can provide the information stored in the reserved address space 304 of the firmware register 202 to the host device 102, the baseboard management controller 206, or other devices connected to the electronic system 100. In addition, the host device 102, the baseboard management controller 206, or another device connected to the electronic system 100 can also retrieve information with regard to the temperature state, a debug state, a S.M.A.R.T warning state, or another instance of the system health information 218 of FIG. 2 from the firmware register 204.

The local system health monitor 202 can use the unreserved address space 304 of the TSE2002av or TSE 2004av compliant temperature register for any device information retrieval purpose. In one specific embodiment, the system health monitor 202 can use the unreserved address space 304 of the TSE 2002av or TSE 2004av to control a set of LED lights to indicate a device health, store information concerning a device inventory, or isolate a faulty device from a system chassis.

Figure 7:
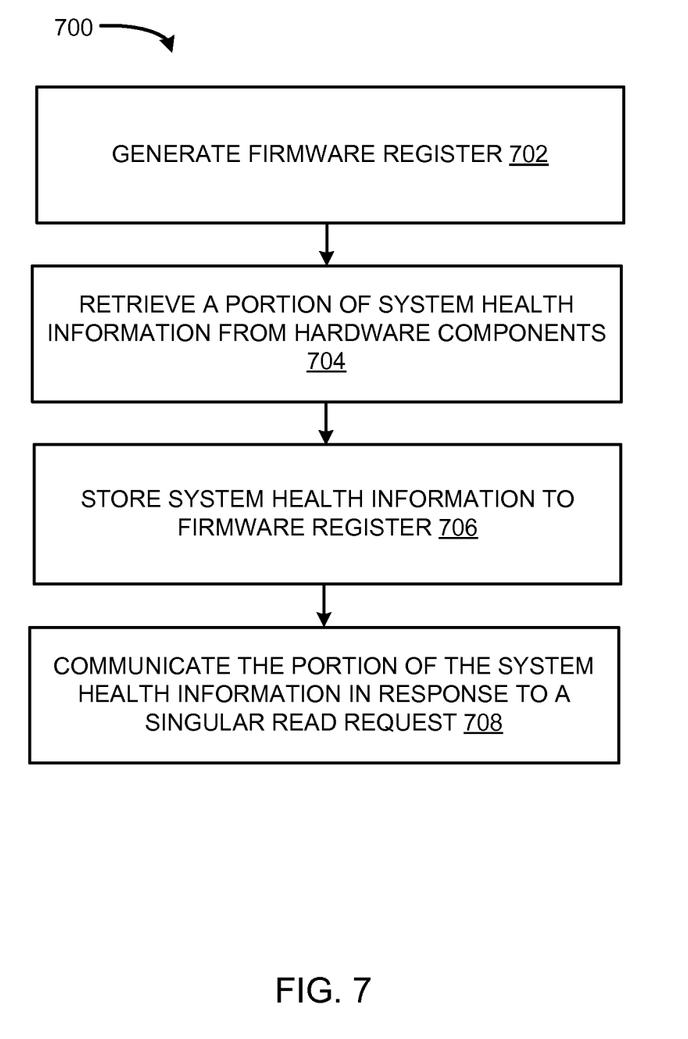
FIG. 7 is a flow chart of a method of operation of the electronic system in a further embodiment of the present invention.

Referring now to FIG. 7, therein is shown an example of a flow chart of a method 700 of operation of the electronic system 100 of FIG. 1 in a further embodiment. In one example embodiment, the electronic system 100 can implement the control flow 500 of FIG. 5.

The method 700 can include generating, with the control unit 212 of FIG. 2, the firmware register 204 of FIG. 2 in a block 702; retrieving, with the communication unit 216 of FIG. 2, at least a portion of the system health information 218 of FIG. 2 in a block 704; storing, with the control unit 212, the system health information 218 to the firmware register 204 in a block 706; and communicating, with the communication unit 216, the portion of the system health information 218 in response to the singular read request 220 of FIG. 2 independent of the operational status 222 of FIG. 2 of the host device 102 of FIG. 1 in a block 708.

The steps described herein can be implemented in hardware including as hardware accelerators, passive circuitry, active circuitry, or a combination thereof, in the control unit 212. The steps can also be implemented in hardware including as hardware accelerators, passive circuitry, active circuitry, or a combination thereof, within the host device 102, the monitored device 106, or a combination thereof but outside of the control unit 212.

For illustrative purposes, the various steps have been described as being specific to the host device 102, the monitored device 106, or a combination thereof. However, it is understood that the steps can be distributed differently. For example, the various steps can be implemented in a different device, or the functionalities of the steps can be distributed across multiple devices. Also as an example, the various steps can be stored in a non-transitory memory medium.

As a more specific example, one or more steps described above can be stored in the non-transitory memory medium for distribution to a different system, a different device, a different user, or a combination thereof. Also as a more specific example, the steps described above can be implemented or stored using a single hardware unit, such as a chip or a processor, or across multiple hardware units.

The steps described in this application can be stored in the non-transitory computer readable medium. The storage unit 214 of FIG. 2, the memory 232 of FIG. 2, or a combination thereof can represent the non-transitory computer readable medium. The storage unit 214, the memory 232, or a combination thereof, or a portion therein can be removable from the monitored device 106. Examples of the non-transitory computer readable medium can be a non-volatile memory card or stick, an external hard disk drive, a tape cassette, or an optical disk.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of the embodiment of the present invention is that it valuably supports and services the historical trend of reducing costs, simplifying systems, and increasing performance. These and other valuable aspects of the embodiment of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. An electronic system, comprising:
    a communication unit configured to retrieve at least a portion of a system health information from hardware components of a monitored device, and communicate the portion of the system health information in response to a singular read request independent of an operational status of a host device;
    a control unit, coupled to the communication unit, configured to:
        generate a firmware register on the monitored device, and store the system health information to the firmware register; and
        manage the hardware components independent of the operational status of the host device based on the system health information.

2. The system as claimed in claim 1 wherein the communication unit is configured to retrieve the portion of the system health information by multiple reads of the hardware components.

3. The system as claimed in claim 1 wherein the communication unit is configured to retrieve the portion of the system health information by accessing or querying the hardware components sequentially or serially.

4. The system as claimed in claim 1 wherein the control unit is configured to generate the firmware register by emulating a reserved address space for the host device.

5. The system as claimed in claim 1 wherein the communication unit is configured to communicate the portion of the system health information to the host device.

6. The system as claimed in claim 1 wherein the control unit is configured to manage the hardware components independent of the operational status of the host device by shutting down, rebooting, power cycling, debugging, or a combination thereof of the hardware components.

7. The system as claimed in claim 1 wherein the communication unit is configured to retrieve the portion of the system health information by retrieving the portion of the system health information based on an event trigger, a timer, or a combination thereof.

8. The system as claimed in claim 1 wherein the firmware register includes a temperature register.

9. A method of operation of an electronic system comprising:
    generating, with a control unit, a firmware register on a monitored device;
    retrieving at least a portion of a system health information from hardware components of the monitored device;
    storing the system health information to the firmware register;
    managing the hardware components independent of the operational status of a host device based on the system health information; and
    communicating, with a communication unit, the portion of the system health information in response to a singular read request independent of an operational status of the host device.

10. The method as claimed in claim 9 wherein retrieving the portion of the system health information includes retrieving the portion of the system health information from multiple reads of the hardware components.

11. The method as claimed in claim 9 wherein retrieving the portion of the system health information includes retrieving the portion of the system health information by accessing or querying the hardware components sequentially or serially.

12. The method as claimed in claim 9 wherein generating the firmware register includes emulating a reserved address space for the host device in the firmware register.

13. The method as claimed in claim 9 wherein communicating the portion of the system health information includes communicating the portion of the system health information to the host device.

14. The method as claimed in claim 9 wherein managing the hardware components includes shutting down, rebooting, power cycling, debugging, or a combination thereof of the hardware components.

15. The method as claimed in claim 9 wherein retrieving the portion of the system health information includes retrieving the portion of the system health information based on an event trigger, a timer, or a combination thereof.

16. The method as claimed in claim 9 wherein generating the firmware register includes emulating a temperature register.

17. A non-transitory computer readable medium including instructions for execution, comprising instructions for:
    generating a firmware register on a monitored device;
    retrieving at least a portion of a system health information from hardware components of a monitored device;
    storing the system health information to the firmware register;
    managing the hardware components independent of the operational status of a host device based on the system health information; and
    communicating the portion of the system health information in response to a singular read request independent of an operational status of the host device.

18. The non-transitory computer readable medium as claimed in claim 17 wherein retrieving the portion of the system health information includes retrieving the portion of the system health information from multiple reads of the hardware components.

19. The non-transitory computer readable medium as claimed in claim 17 wherein retrieving the portion of the system health information includes retrieving the portion of the system health information by accessing or querying the hardware components sequentially or serially.

20. The non-transitory computer readable medium as claimed in claim 17 wherein generating the firmware register includes emulating a reserved address space for the host device in the firmware register.

\* \* \* \* \*